United States Patent [19]

Franks

[11] Patent Number: 4,510,386

[45] Date of Patent: * Apr. 9, 1985

[54] THINNING OF SPECIMENS FOR EXAMINATION UNDER THE ELECTRON MICROSCOPE

[75] Inventor: Joseph Franks, London, England

[73] Assignee: Ion Tech Limited, Middlesex, England

[ * ] Notice: The portion of the term of this patent subsequent to Jul. 20, 1999 has been disclaimed.

[21] Appl. No.: 362,531

[22] Filed: Mar. 29, 1982

[30] Foreign Application Priority Data

Mar. 31, 1981 [GB] United Kingdom ................ 8110073

[51] Int. Cl.³ .............................................. G01N 1/32
[52] U.S. Cl. ..................................... 250/251; 250/311
[58] Field of Search ................................. 250/311, 251

[56] References Cited

U.S. PATENT DOCUMENTS 3,657,542  4/1972  Futch, Jr. et al. ................ 250/251
4,128,765 12/1978  Franks .......................... 250/398 X
4,284,952  8/1981  Fink ............................. 250/251 X
4,340,815  7/1982  Franks .......................... 250/311 X Primary Examiner—Alfred E. Smith
Assistant Examiner—Jack I. Berman
Attorney, Agent, or Firm—Irvin A. Lavine

[57] ABSTRACT

Heretofore specimens have been thinned to penetration for examination by electron microscopy techniques, by ion erosion techniques. Such technique finds particular suitability to eroding materials made of glass, ceramics, and geological specimens which cannot be treated by chemical etchants. The present disclosure while acknowledging the advances which ion erosion techniques have made in this field, is concerned with a more rapid technique employing a beam or beams comprised solely of neutral particles. In tests carried out using this technique the sputtering rate from a sample specimen has been shown to be several percentages greater using a neutral source than from an ion source with the same flux density.

7 Claims, 3 Drawing Figures

THINNING OF SPECIMENS FOR EXAMINATION UNDER THE ELECTRON MICROSCOPE

FIELD OF THE INVENTION

The present invention relates to specimen thinning techniques for the preparation of materials for examination under the electron microscope.

BACKGROUND ART

The high resolution attainable with transmission electron microscopy makes this an outstanding technique for examining the microstructure of materials. The direct examination of materials by transmission electron microscopy requires that the specimen to be examined is transparent to electrons. Consequently the thickness of the specimens must be restricted to 100 to 200 nm.

It has therefore been necessary to develop methods for preparing thin specimens of materials that have widely varying mechanical and chemical properties. Soft materials such as biological specimens may be prepared by microtoming, although difficulty is sometimes encountered when hard particles are present.

For some metals, semiconductors, and other inorganic materials, chemical etching and electrolytic techniques are suitable. In one widely used method the material to be thinned is placed in a jet etching tank and the etching process observed through a lens with a light source behind the specimen.

The etching action of the jet is maintained until perforation of the specimen occurs. Since the etching action is stronger at the centre of the jet than its periphery, perforation starts at the centre and spreads towards the periphery. Thus the etching process is immediately arrested when perforation occurs by flushing the specimen with an inhibiting wash, leaving adjacent areas around the perforation which are usually sufficiently thin to allow micrographs to be taken during examination under the electron microscope.

For materials for which suitable chemical etchants do not exist, such as some glasses, ceramics, and geological specimens, various mechanical preparation techniques have been tried. The specimens may be crushed and fine slivers selected, or thin sections may be produced by very careful mechanical polishing. These operations require considerable skill and can generally not be applied to brittle granular materials with voids.

A large variety of materials which do not lend themselves to chemical treatment may be thinned by ion erosion.

In typical known thinning equipment ion beams of about 2 mm diameter from two sources impinge centrally on either side of a specimen. See Franks U.S. Pat. No. 4,128,765. A hole or perforation is allowed to form in the specimen by the ion beam, which acts in a similar way to the chemical jet during chemical etching, when the ion beam is immediately turned off to leave adjacent thin areas around the perforation transparent to electrons. Such method and apparatus is shown in Franks U.S. Pat. No. 4,340,815.

Ion erosion has proved an increasingly valuable tool to electron microscopists especially those engaged in examining classes of material such as ceramics, impurity-doped semiconductors and alloys.

Difficulty however arises when dealing with ionic and covalent materials since bombardment with the charged particles of the ion beam may deleteriously affect the structure of the material.

SUMMARY OF THE INVENTION

It is an object of the invention to provide a method of thinning specimens by particle bombardment of the specimen, which method obviates the deficiencies of known ion erosion techniques when dealing with ionic and covalent materials.

According to the invention there is provided a method of preparing specimens suitable for examination by electron microscopy techniques comprising providing a source for producing a beam of energetic uncharged or neutral particles, and irradiating a specimen by the beam thereby to erode the specimen to penetration and produce an area surrounding the penetration of suitable thickness for transmission of electrons.

The method of thinning specimens as afforded by the present invention with a neutral beam is particularly advantageous when dealing with ionic and covalent materials since the absence of surface charge reduces migration of any mobile charge constituent of the material being thinned.

Thinning of the specimen using a neutral beam source may be carried outby using two neutral beams, one on either side of the specimen, and thinning to penetration. A more rapid technique may be employed by using one source with the specimen position close to the beam aperture of the source where the intensity and hence the eroding power of the neutral particle beam is the greater.

Any source which is capable of producing a beam of charged particles which can then be neutralised before impinging on the specimen would be suitable, such sources being well known to those skilled in the art.

For example, ions may be passed through a resonance charge exchange tube and the resulting neutral beam allowed to impinge on the specimen. A preferred technique is to use a saddle field source with a neutral output which eliminates the cumbersome charge exchange tube.

Other features and advantages of the present invention will become apparent from the description that follows.

BEST MODES OF CARRYING OUT THE INVENTION

As mentioned earlier the technique for thinning specimens for use in electron microscopy by ion erosion is known, and the saddle field ion source is suitable for providing the neutral beam required to perform the present invention.

Figure 1:
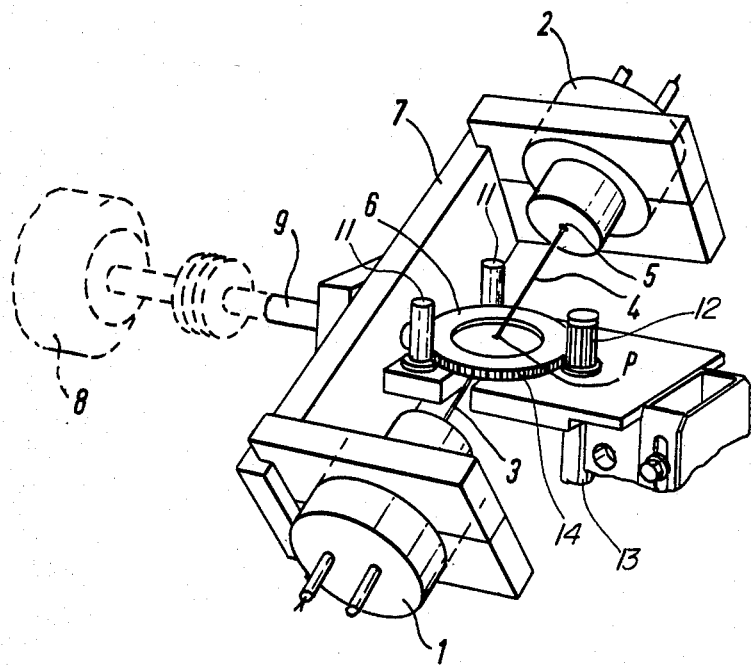
FIG. 1 is a perspective view of a thinning unit for emitting a beam of neutral particles, in accordance with the present invention.

A thinning unit for thinning specimens with a neutral beam is shown in FIG. 1. It comprises two fine beam netural saddle field sources 1 and 2 which produce neutral beams 3 and 4 of about 1½ mm. diameter from the cathode apertures 5.

The neutral beams are directed to pass through the centre of a rotatable specimen platform 6 the centre P of which is located on the axis of the pivot of an arm 7 which supports the two sources 1 and 2.

The arm 7 is driven by a servo motor 8 through a rotary shaft 9. The rotatable arm 7 may be set an an angle relative to the plane of the specimen platform 6 from 0° (glancing incidence) through 90° (normal) to 180° and may be rocked at any amplitude between these limits.

The specimen 10 is mounted on the rotatable specimen platform 6, which is supported on rollers 11, and driven by shaft 13 of a motor (not shown) through a gear wheel 12 which meshes with teeth on the peripheral edge 14 of the platform 6.

During a thinning process material is controllably removed from either side of the specimen by exposure to the neutral beams from the two diammetrically opposed sources 1 and 2.

The specimen is illuminated and may be observed during processing through a binocular microscope (not shown) mounted above the unit.

Although thinning of the specimen using the unit as described with a neutral beam may be carried out by using two neutral beam sources, one on either side of the specimen with the specimen held normally at 2 cm. from the aperture of the source, a more rapid technique may be employed by using only one source with the specimen positioned as close as possible to the beam aperture (commensurate with the possibility of insertion and removal of the specimen between the source and the specimen platform 6) where the intensity, and hence the eroding power of the neutral particle beam, is the greater. In practice the preferred beam power of the source is within the range 4 to 8 kV at a plasma current of up to ½ mA.

Figure 2:
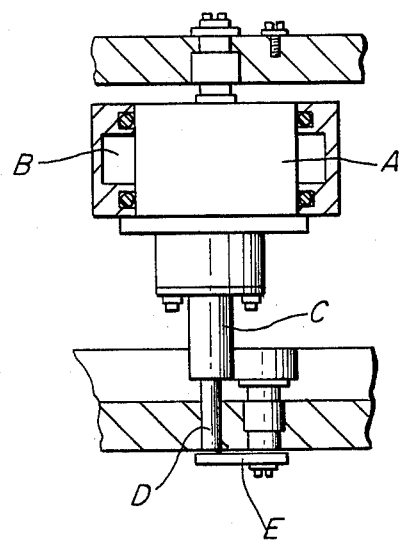
FIG. 2 is an elevational view of apparatus useful with the present invention.

The thinning apparatus shown in FIG. 2 comprises ion source A of the saddle field type surrounded by a water cooling jacket B. The saddle field source is provided with a cathode C from which emerges a beam of atoms when the source is energized. The specimen carrier D bearing a specimen is placed in the path of the beam emerging from the cathode aperture of the cathode C, so that over a period of time the beam penetrates the specimen.

The specimen is held in close proximity spacing with respect to the cathode aperture and preferably with a critical range of 2 cm therefrom. A detector plate E is mounted behind the specimen carrier D, and when the specimen has been penetrated by the beam, the detector plate E senses such penetration as a result of a current produced by secondary electron emission from plate E.

Figure 3:
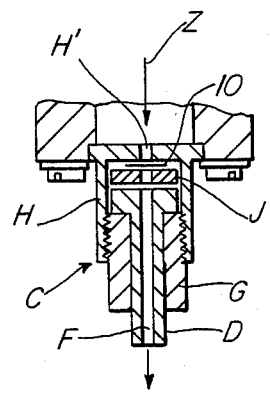
FIG. 3 is a longitudinal cross-sectional view of a part of the structure shown in FIG. 2.

FIG. 3 shows the cathode C of the arrangement of FIG. 2 is cross-sectional detail and wherein a specimen 10 is shown positioned normal to the direction of the atom beam Z. The specimen carrier D is held within a cathode housing H by means of a carrier insert G. The cathode housing has a cathode aperture H', from which emerges the beam Z. The insert G is screw mounted for adjustment in the housing H, so that the specimen can be positioned at the required distance from the aperture H'. The carrier D has a passage F positioned to be in alignment with the beam Z so that the plate E is able to determine the presence of the beam when penetration of the specimen 10 has occurred.

A flat spacer plate J is provided for mounting the specimen 10 normal to the atom beam Z and in front of the cathode aperture H' of the cathode C.

Thinning insulating specimens using a beam comprised solely of neutral particles is more rapid than with an ion beam or a beam comprised of a mixture of ions and neutrals of the same energy and flux density.

To compare the effects of ion and neutral bombardment on stoichiometry, thin specimens of magnesium oxide were bombarded from one side of a specimen separately with ions and neutrals. With 6 kV applied to a saddle field source, X-ray analysis showed that cation concentration at the unthinned surface under ion bombardment increased by 80%, while under neutral bombardment the increase was 20%. In addition the sputtering rate of the oxide was 15% greater from a neutral source than from an ion source with the same flux density.

To explain this effect it is proposed that the positively charged ions in an ion beam exert electrostatic forces on ions in the sample. The attractive force on the anions will produce an increase in the preferential sputtering of the oxygen ions with an associated creation of a positively charged surface region. The electrostatic repulsive forces from both the beam and the surface will therefore produce a driving force for cations away from the thinned surface.

With a neutral beam these driving forces will be reduced. Some positive surface charge may still remain however because of secondary electron emission.

I claim:

1. A method of preparing specimens suitable for examination by electron micrscopy techniques comprising providing a source for producing a beam consisting substantially exclusively of energetic or neutral particles, and irradiating a specimen by the beam thereby to erode the specimen to penetration and produce an area surrounding the penetration of suitable thickness for transmission electrons.

2. A method as claimed in claim 1 wherein the specimen is held as close as possible to the aperture of the source where the intensity and hence eroding power of the neutral beam is the greater thereby to rapidly thin the specimen to penetration.

3. A method as claimed in claim 1 wherein a pair of said neutral beam sources are employed to act on either side of the specimen respectively to thin the specimen to penetration.

4. A method as claimed in claim 1 wherein the source is a saddle field source.

5. Apparatus for preparing specimens suitable for examination by electron microscopy techniques comprising a platform for supporting a specimen, and a source for producing a beam consisting substantially exclusively of neutral particles arranged with respect to the specimen such that in use, the beam produced by the source is directed onto the specimen to thereby thin the specimen to penetration.

6. Apparatus as claimed in claim 5 wherein a said source is positioned on either side of the specimen so that the beams therof are directable onto the specimen to thin one part thereof to penetration.

7. Apparatus as claimed in claim 5 wherein the source is a saddle field ion source modified to produce a beam of neutral particles.

* * * * *